United States Patent [19]

Malz, Jr. et al.

[11] Patent Number: 4,607,104

[45] Date of Patent: Aug. 19, 1986

[54] PROCESS FOR THE PRODUCTION OF 2,2,6,6-TETRAALKYL-4-PIPERIDYLAMINES

[75] Inventors: Russell E. Malz, Jr., Naugatuck; Harold Greenfield, Watertown, both of Conn.

[73] Assignee: Uniroyal Chemical Company, Inc., Middlebury, Conn.

[21] Appl. No.: 754,378

[22] Filed: Jul. 11, 1985

[51] Int. Cl.$^4$ .................. C07D 401/12; C07D 401/14
[52] U.S. Cl. ..................................... 546/186; 546/189; 546/191; 546/223; 546/244
[58] Field of Search ............... 546/186, 189, 191, 223, 546/244

[56] References Cited

U.S. PATENT DOCUMENTS

| | | | |
|---|---|---|---|
| 4,104,248 | 8/1978 | Cantatore | 260/45.8 N |
| 4,326,063 | 4/1982 | Son | 546/191 |
| 4,415,688 | 11/1983 | Minagawa et al. | 524/102 |

FOREIGN PATENT DOCUMENTS 3007996  9/1981  Fed. Rep. of Germany ...... 546/186

OTHER PUBLICATIONS

P. N. Rylander, Catalytic Hydrogenation Over Platinum Metals, pp. 12-13, Academic Press (1967).
P. N. Rylander, Catalytic Hydrogenation in Organic Syntheses, pp. 3-4, Academic Press (1979).
M. Freifelder, Catalytic Hydrogenation in Organic Synthesis Procedures and Commentary, p. 3, Wiley and Sons.
M. Freifelder, Practical Catalytic Hydrogenation, pp. 81-82, Wiley and Sons.

*Primary Examiner*—Robert T. Bond
*Attorney, Agent, or Firm*—Willian E. Dickheiser

[57] ABSTRACT

2,2,6,6-tetraalkyl-4-piperidylamines are produced by reacting an amine with a 2,2,6,6-tetraalkyl-4-piperidone in the presence of a catalyst selected from the group consisting of platinum, nickel and cobalt, employing a reaction medium comprising (a) between about 10 and 100 weight percent water and (b) between 0 and about 90 weight percent of a polar organic compound selected from the group consisting of $C_1$-$C_{10}$ aliphatic alcohols and $C_2$-$C_6$ aliphatic glycols.

16 Claims, No Drawings

PROCESS FOR THE PRODUCTION OF 2,2,6,6-TETRAALKYL-4-PIPERIDYLAMINES

FIELD OF THE INVENTION

This invention is directed to an improved process for the production of 2,2,6,6-tetraalkyl-4-piperidylamines, which process involves the use of a platinum, nickel or cobalt catalyst in a reaction medium comprising (a) between about 10 and 100 weight percent water and (b) between 0 and about 90 weight percent of at least one polar organic compound selected from the group consisting of $C_1$–$C_{10}$ aliphatic alcohols and $C_2$–$C_6$ aliphatic glycols.

BACKGROUND OF THE INVENTION

The use of 2,2,6,6-tetraalkyl-4-piperidylamines, such as N,N'-bis(2,2,6,6-tetramethyl-4-piperidyl)hexamethylenediamine, as ultraviolet stabilizers for polymeric materials is well known in the art. In the past, the production of these compounds has generally involved the use of a platinum, nickel or cobalt catalyst in an aliphatic alcohol solvent.

Thus, U.S. Pat. No. 4,104,248 issued to G. Cantatore shows the production of N,N'-bis(2,2,6,6-tetramethyl-4-piperidyl)ethylenediamine employing a platinum or carbon catalyst and utilizing methanol as a reaction medium. Similarly, U.S. Pat. No. 4,326,063 issued to P. N. Son discloses a process for producing 2,2,6,6-tetraalkyl-4-piperidylaminocycloalkyl compounds utilizing a platinum catalyst and a polar organic solvent, such as an aliphatic (lower alkyl) alcohol, while Minagawa et al in U.S. Pat. No. 4,415,688 show the production of certain 2,2,6,6-tetraalkylpiperidylamine compounds employing a platinum/carbon catalyst and methanol as the solvent.

Somewhat similarly, in German Offenlegungschrift No. 3,007,996, a Raney nickel or cobalt catalyst is employed in an inert organic solvent to produce polyalkylpiperidylamines.

Although such prior art process will produce 2,2,6,6-tetraalkyl-4-piperidylamines in desirable yields, the pyrophoric nature of the platinum, nickel or cobalt catalysts utilized coupled with the flammable solvents employed present a potential hazard. Thus, P. N. Rylander, *Catalytic Hydrogenation Over Platinum Metals*, page 12, Academic Press (1967), has stated "Platinum metal catalysts are generally nonpyrophoric and can be safely held in the hand. However, they catalyze the oxidation of organic compounds and great care must be taken when the catalysts are brought into contact with organic liquids or combustible vapors. Platinum metal catalysts, especially platinum or palladium, are prone to ignite lower alcohols." Moreover, the same author has cautioned, in *Catalytic Hydrogenation in Organic Syntheses*, page 3, Academic Press (1979), that "Virgin catalysts, such as Raney nickel, which contain dissolved hydrogen ignite when exposed to air, and due care should be taken in handling . . . " and, further, that "Metal catalysts on finely divided carbon are subject to dust explosions, just as carbon itself or flour is." Consequently, it would be desirable to possess a process for producing 2,2,6,6-tetraalkyl-4-piperidylamines which process would avoid the potential health hazard associated with such prior art processes.

As is discussed in some detail below, the mechanism of the reaction between amines and 2,2,6,6-tetraalkyl-4-piperidones in the production of 2,2,6,6-tetraalkyl-4-piperidylamines involves an equilibrium reaction between (A) an alkanolamine on one hand and (B) a ketimine and water on the other, with the ketimine subsequently being hydrogenated to form the product 2,2,6,6-tetraalkyl-4-piperidylamine.

Therefore, it is completely unexpected that the use of a reaction medium comprising at least about 10 weight percent water in the platinum, nickel or cobalt catalyzed production of 2,2,6,6-tetraalkyl-4-piperidylamines would not only reduce the threat of flammability presented by such pyrophoric catalysts, but would additionally not materially affect the amount of substituted piperidylamine produced.

DESCRIPTION OF THE INVENTION

The present invention is directed to a process for producing compounds of the formula:

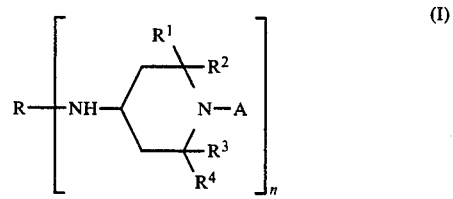

wherein:

R is $C_1$–$C_{18}$ alkyl, $C_5$–$C_6$ cycloalkyl or $C_7$–$C_9$ aralkyl;

$R^1$, $R^2$, $R^3$ and $R^4$ are the same or different and are $C_1$–$C_8$ alkyl;

A is hydrogen, hydroxy, $C_1$–$C_8$ alkoxy, $C_1$–$C_8$ alkyl, $C_2$–$C_{10}$ alkylcarbonyl or arylcarbonyl; and n is 1, 2, 3 or 4;

with the proviso that when n is 2, 3, or 4, the $R^1$, $R^2$, $R^3$, $R^4$ and A substituents of the pyridine rings may each independently be different members within the scope of their definitions;

which process comprises reacting an amine of the formula $R(NH_2)_n$, wherein R and n are as defined above, with at least one 2,2,6,6-tetraalkyl-4-piperidone of the formula:

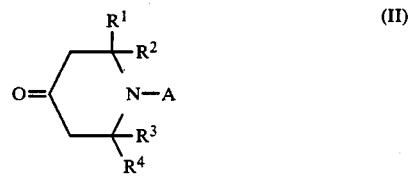

wherein A, $R^1$, $R^2$, $R^3$ and $R^4$ are as defined above; in the presence of a catalyst selected from the group consisting of platinum, nickel and cobalt, employing a reaction medium comprising (a) between about 10 and 100 weight percent water and (b) between 0 and about 90 weight percent of at least one polar organic compound selected from the group consisting of $C_1$–$C_{10}$ aliphatic alcohols and $C_2$–$C_6$ aliphatic glycols.

As is employed herein, terms such as "2,2,6,6-tetraalkyl-4-piperidylamine" are intended to encompass compounds having substituents bonded to the piperidinyl nitrogen (i.e., "A" substituents).

Moreover, it is to be noted that when n in formula I above is 2, 3, or 4, the $R^1$, $R^2$, $R^3$, $R^4$ and A substituents of the piperidine rings may each independently be different members within the scope of their definitions. Thus, when 2 or more piperidinyl rings are pendent from the resultant compound, the substituents off each of the rings may be different. For example, if n is two, A may be both hydrogen and hydroxyl—i.e., the compound is both 2,2,6,6-tetraalkyl-4-piperidinylamino and 1-hydroxy-2,2,6,6-tetraalkyl-4-piperidinylamino substituted.

Illustrative of the amines which may be employed are aliphatic mono-, di-, tri- and tetramino alkyl amines such as methylamine, butylamine, dodecylamine, octadecylamine, triethylenediamine, tetraethylenediamine, hexamethylenediamine, dipropylenetriamine, diethylenetriamine, 1,2,6-triaminohexane and the like; arylamines such as aniline, phenylenediamine and the like; and aralkylamines such as benzylamine and the like. Preferred amines are hexamethylenediamine and tetramethylenediamine.

Suitable 4-piperidones which can be used in the process of this invention include 2,2,6,6-tetramethyl-4-piperidone; 1,2,2,6,6-pentamethyl-4-piperidone; 1-ethyl-2,2,6,6-tetramethyl-4-piperidone; 1-n-octyl-2,2,6,6-tetramethyl-4-piperidone; 2,6-diethyl-2,6-dimethyl-4-piperidone; 2-isobutyl-2,6,6-trimethyl-4-piperidone; 1-acetyl-2,2,6,6-tetramethyl-4-piperidone; 1-benzoyl-2,2,6,6-tetramethyl-4-piperidone; 1-hydroxy-2,2,6,6-tetramethyl-4-piperidone; 1-methoxy-2,2,6,6-tetramethyl-4-piperidone; and the like. The preferred 4-piperidone is 2,2,6,6-tetramethyl-4-piperidone.

Many of such suitable 4-piperidones are known compounds, the preparation of which can be found in the literature. For example, Francis, J. Chem. Soc., 2897 (1927), discloses a process for the preparation of triacetoneamine, another name for 2,2,6,6-tetramethyl-4-piperidone (where A is hydrogen); Biel & Robertson, U.S. Pat. No. 3,364,220, Example 9, show the preparation of 1,2,2,6,6-pentamethyl-4-piperidone (where A is methyl); Rozantsev and Golubev, Chem. Abs. 65, 10559 (1966), show the preparation of 1-hydroxy-2,2,6,6-tetramethyl-4-piperidone (where A is hydroxy); and Holt, U.S. Pat. No. 3,734,883, column 2 lines 1-18, shows the preparation of these compounds where A is methyl. Other compounds within the scope of formula (II) can be prepared similarly.

The catalyst employed in the process of this invention is selected from the group consisting of platinum, nickel and cobalt. Such catalyst may be employed in the form of a bulk metal or metal oxide. Preferably such catalyst is supported on a suitable carrier. Illustrative of carriers which may be employed are carbon, alumina and kielsguhr. Sulfided forms of the catalyst may also be employed. The preferred catalyst is platinum.

The reaction medium of the process of this invention comprises (a) between about 10 and 100 weight percent water and (b) between 0 and about 90 weight percent of at least one polar organic compound selected from the group consisting of $C_1$–$C_{10}$ aliphatic alcohols and $C_2$–$C_6$ aliphatic glycols. Preferred reaction media include water, mixtures of 2-propanol with water, mixtures of isopropanol and water and mixtures of methanol with water.

The reaction mechanism of the process of this invention may be diagrammed as follows (wherein R, $R^1$, $R^2$, $R^3$, $R^4$ and A are as defined above):

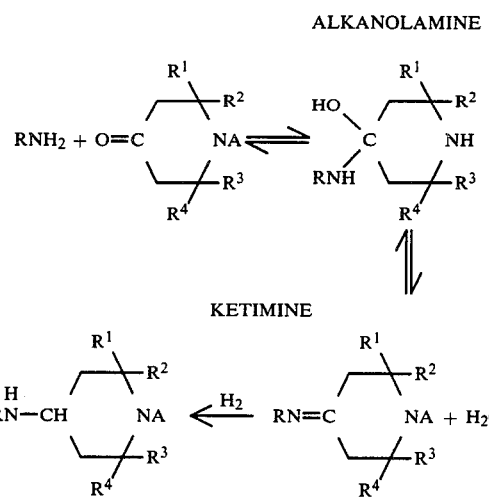

From the equilibrium reaction above, one would assume that the presence of a relatively large percentage of water (i.e., about 10 weight percent or more) would shift the equilibrium away from the ketimine towards the alkanolamine intermediate and would therefore result in a poor yield of product. However, as is shown in the Examples below, this shifting of the equilibrium (if indeed such shifting occurs at all) unexpectedly does not substantially affect the total yield of product produced.

The process of this invention is typically performed as follows. The amine, the 2,2,6,6-tetraalkyl-4-piperidone, reaction medium and catalyst are all charged to the reactor, which is generally a pressure vessel.

The equivalent ratio of piperidone per amine functional group is most preferably within the range of from 1:1 to 1.2:1.

The ratio of reagents to solvent (i.e., reaction medium) is not critical, and typically solvent will comprise between about 5 and about 80 weight percent of the entire reaction mixture.

As is well known to those skilled in the art, for batch reactions the catalyst concentration may vary greatly depending on factors such as reaction temperature, reaction pressure and desired cycle time.

Once the reaction mixture has been introduced to the reaction vessel, the vessel is typically pressurized with hydrogen and, generally, is heated to reaction temperature. The reaction temperature may range between about 15° C. and about 100° C., is preferably between about 45° C. and about 90° C., and is most preferably between about 60° C. and about 85° C. Reaction pressure may range from about 15 to about 2,000 psi, and is preferably between about 50 and 900 psi. Most preferably, the reaction is conducted at between about 100 and about 750 psi.

The reaction time will vary in accordance with factors such as reaction batch size, reaction temperature, reaction pressure, the particular reactants selected and the like. If desired, the progress of the reaction may be followed by monitoring the hydrogen absorption.

Once the reaction has proceeded to the desired extent, the reactor is typically cooled and depressurized. Recovery of the product is typically carried out by first filtering off catalyst, then removing solvent and impurities, including unreacted starting ingredients, from the product by distillation.

By making modifications readily apparent to those skilled in the art, the process of this invention may be carried out in a batch or continuous manner.

EXAMPLES

The following Examples are intended to further illustrate the process of this invention and are not intended to limit the scope of this invention in any manner.

EXAMPLE 1 AND COMPARATIVE EXPERIMENT A

To a one liter autoclave were charged 34.8 grams (0.30 mole) of hexamethylenediamine (HMDA), 97.65 grams (0.63 mole) of 2,2,6,6-tetramethyl-4-piperidone (TAA), 120 ml of the reaction medium (water in Example 1; methanol in Comparative Experiment A) and 1.5 grams of a 5% platinum on carbon catalyst. The autoclave was pressurized with hydrogen. After heating to 80° C., pressure was maintained at 600–800 psig.

The reaction products were concentrated on a rotary evaporator at 95° C. and 30 mm Hg. The products were analyzed by quantitative gas liquid chromatography. The results of such analyses are summarized in Table I below.

TABLE I

PREPARATION OF 2,2,6,6-TETRAMETHYL-4-PIPERIDYL-SUBSTITUTED HEXAMETHYLENEDIAMINE

| Example or Comparative Experiment | Catalyst | Solvent | Time, hr. | Yield, mole % | | | | |
|---|---|---|---|---|---|---|---|---|
| | | | | bis[a] | mono[b] | TAA[c] | Alcohol[d] | HMDA |
| 1 | Pt | Water | 2.4 | 89 | 3.1 | 0.43 | 3.2 | N.D.[e] |
| A | Pt | Methanol | 4.8 | 93 | 0.47 | 2.9 | 0.57 | N.D. |

[a] N,N'—bis(2,2,6,6-tetramethyl-4-piperidyl)hexamethylenediamine.
[b] N—(2,2,6,6-tetramethyl-4-piperidyl)hexamethylenediamine.
[c] 2,2,6,6-tetramethyl-4-piperidone.
[d] 2,2,6,6-tetramethyl-4-piperidinol; yield based on starting 2,2,6,6-tetramethyl-4-piperidone.
[e] None detected.

The above data indicate that the process of this invention, employing a reaction medium comprising at least about 10 weight percent water, will produce almost equivalent amounts of 2,2,6,6-tetramethyl-4-piperyl-substituted hexamethylene diamines as will prior art processes employing water as a reaction medium. Thus, in Example 1, a total yield of 92.1 percent (based on theoretical yield) of mono- and bis- substituted compound is obtained employing water as a reaction medium. In comparison, Comparative Experiment A shows that a total of 93.47 percent substituted compound is produced employing methanol as a reaction medium. However, the potential risk presented by the pyrophoric platinum reacting with the methanol reaction medium in Comparative Experiment A is completely eliminated in Example 1.

EXAMPLE 2

To a one-gallon autoclave were added 456.4 grams (2.94 moles) of 2,2,6,6-tetramethyl-4-piperidone, 162.7 grams (1.40 moles) of hexamethylenediamine, 770 ml of water and 28.0 grams of a 5% platinum on carbon catalyst. The autoclave was pressurized with hydrogen. After heating to 80° C., pressure was maintained at 100–200 psig. The reaction was continued for a total of 5.3 hours, which was 1 hour after hydrogen absorption had apparently ceased.

The reactor was cooled to room temperature and the reaction product removed from the reactor. The catalyst was removed from the product by filtration, and the volatiles removed under reduced pressure. Gas liquid chromatographic analysis of the product revealed that a 90 mole percent conversion (based on theoretical yield) to N,N'-bis(2,2,6,6-tetramethyl-4-piperidyl)hexamethylenediamine had been accomplished, thereby demonstrating the efficacy of the process of this invention at comparatively low pressures of 100–200 psig.

What is claimed is:

1. A process for producing compounds of the formula:

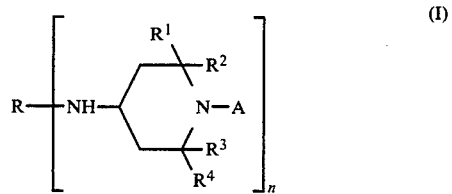

wherein:
R is $C_1$–$C_{18}$ alkyl, $C_5$–$C_6$ cycloalkyl or $C_7$–$C_9$ aralkyl;
$R^1$, $R^2$, $R^3$ and $R^4$ are the same or different and are $C_1$–$C_8$ alkyl;
A is hydrogen, hydroxy, $C_1$–$C_8$ alkoxy, $C_1$–$C_8$ alkyl, $C_2$–$C_{10}$ alkylcarbonyl or arylcarbonyl; and
n is 1, 2, 3 or 4;
with the proviso that when n is 2, 3 or 4, the $R^1$, $R^2$, $R^3$, $R^4$ and A substituents of the piperidine rings may each independently be different members within the scope of their definitions;
which process comprises reacting an amine of the formula $R(NH_2)_n$, wherein R and n are as defined above, with at least one 2,2,6,6-tetraalkyl-4-piperidone of the formula:

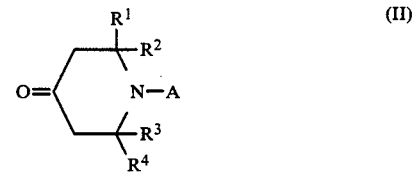

wherein A, $R^1$, $R^2$, $R^3$ and $R^4$ are as defined above; in the presence of a catalyst selected from the group consisting of platinum, nickel and cobalt employing a reaction medium comprising (a) between about 10 and 100 weight percent water and (b) between 0 and about 90 weight percent of at least one polar organic compound selected from the group consisting of $C_1$–$C_{10}$ aliphatic alcohols and $C_2$–$C_6$ aliphatic glycols.

2. The process of claim 1 wherein the reaction medium comprises water and at least one polar organic compound selected from the group consisting of $C_1$–$C_{10}$ aliphatic alcohols and $C_2$–$C_6$ aliphatic glycols.

3. The process of claim 2 wherein the reaction medium is a mixture of water and 2-propanol.

4. The process of claim 2 wherein the reaction medium is mixture of ethanol and water.

5. The process of claim 2 wherein the reaction medium is a mixture of methanol and water.

6. The process of claim 1 wherein said reaction medium comprises water.

7. The process of claim 1 wherein said catalyst is platinum.

8. The process of claim 1 wherein $R^1$, $R^2$, $R^3$ and $R^4$ are methyl and A is hydrogen.

9. The process of claim 8 wherein said amine is selected from the group consisting of methylamine, butylamine, dodecylamine, octadecylamine, cyclohexylamine, benzylamine, triethylenediamine, tetraethylenediamine, hexamethylenediamine, 1,12-diaminododecane, dipropylenetriamine, diethylenetriamine, 1,2,6-triaminohexane, and 1,4-diaminocyclohexane.

10. The process of claim 8 wherein said amine is tetraethylenediamine or hexamethylenediamine.

11. The process of claim 1 wherein the reaction is performed at between about 15 and about 2000 psi.

12. The process of claim 11 wherein the reaction is performed at between about 50 and about 900 psi.

13. The process of claim 12 wherein the reaction is performed at between about 100 and about 750 psi.

14. The process of claim 1 wherein the reaction is performed at between about 15° and about 100° C.

15. The process of claim 14 wherein the reaction is performed at between about 45° and about 90° C.

16. The process of claim 15 wherein the reaction is performed at between about 60° and about 85° C.

* * * * *